US011034932B2

(12) United States Patent
Gao et al.

(10) Patent No.: US 11,034,932 B2
(45) Date of Patent: Jun. 15, 2021

(54) COMPOSITION CAPABLE OF PROMOTING THE GROWTH OF DENITRIFYING MICROORGANISMS AND USES THEREOF

(71) Applicants: CHINA PETROLEUM & CHEMICAL CORPORATION, Beijing (CN); Fushun Research Institute of Petroleum and Petrochemicals, SINOPEC CORP., Liaoning (CN)

(72) Inventors: Huijie Gao, Liaoning (CN); Danfeng Sun, Liaoning (CN); Zhihua Guo, Liaoning (CN); Mingxiang Chen, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC CORP., Liaoning (CN)

( * ) Notice: Subject to any disclaimer, the term of this patent is extended or adjusted under 35 U.S.C. 154(b) by 91 days.

(21) Appl. No.: 15/822,280

(22) Filed: Nov. 27, 2017

(65) Prior Publication Data
US 2018/0148681 A1 May 31, 2018

(30) Foreign Application Priority Data
Nov. 29, 2016 (CN) .......................... 201611073729.7

(51) Int. Cl.
C12N 1/20 (2006.01)
C02F 3/30 (2006.01)
C12N 1/38 (2006.01)
C02F 101/16 (2006.01)

(52) U.S. Cl.
CPC ................ C12N 1/20 (2013.01); C02F 3/305 (2013.01); C12N 1/38 (2013.01); C02F 2101/16 (2013.01); C02F 2101/163 (2013.01); C02F 2101/166 (2013.01); C02F 2203/004 (2013.01); C02F 2305/06 (2013.01)

(58) Field of Classification Search
CPC ... C12N 1/20; C12N 1/38; C02F 3/305; C02F 2305/06; C02F 2203/004; C02F 2101/166; C02F 2101/163; C02F 2101/16
See application file for complete search history.

(56) References Cited

U.S. PATENT DOCUMENTS

| 6,569,334 B1 | 5/2003 | Yoneda | |
| 2013/0319936 A1* | 12/2013 | Sperandio | C02F 3/308 210/605 |
| 2014/0273150 A1* | 9/2014 | Angel | C02F 3/342 435/186 |
| 2019/0119707 A1* | 4/2019 | Boundy-Mills | C12P 19/44 |

FOREIGN PATENT DOCUMENTS

| CN | 1800053 A | 7/2006 |
| CN | 101712943 A | 5/2010 |
| CN | 101898828 A | 12/2010 |
| CN | 102465103 A | 5/2012 |
| CN | 102465104 A | 5/2012 |
| CN | 102465105 A | 5/2012 |
| CN | 102465106 A | 5/2012 |
| CN | 102689982 A | 9/2012 |
| CN | 103058392 A | 4/2013 |
| CN | 103103141 A | 5/2013 |
| CN | 103103142 A | 5/2013 |
| CN | 104940446 A | 9/2015 |
| CN | 105621611 A | 6/2016 |
| CN | 106012527 A | 10/2016 |
| CN | 106554077 A | 4/2017 |
| CN | 106745727 A | 5/2017 |
| CN | 106754450 A | 5/2017 |
| JP | 2003001292 A * | 1/2003 |
| JP | 2003001292 A | 1/2003 |
| JP | 2008149261 A | 7/2008 |
| JP | 2012232963 A | 11/2012 |

OTHER PUBLICATIONS

Ji, B. et al. Aerobic Denitrification: A Review of Important Advances of the Last 30 Years, 2015, Biotechnology and Bioprocess Engineering, 20, 643-651 (Year: 2015).*
Rossi, F. et al. Nitrate Removal from Wastewater through Biological Denitrification with OGA 24 in a Batch Reactor, 2015, Water, 7, 51-62 (Year: 2015).*
Van der Star, W. et al. Response of Anaerobic Ammonium-Oxidizing Bacteria to Hydroxylamine, 2008, Applied and Environmental Microbiology, 74(14), 4417-4426 (Year: 2008).*
Lipinska, L. et al., Antifungal Activity of *Lactobacillus* sp. Bacteria in the Presence of Xylitol and Galactosyl-Xylitol, 2016, BioMed Research International, vol. 2016, Article ID 5897486, 1-8 (Year: 2016).*
Di Wu et al.; "Synergistic Treatment of Iron Sulfide Laden Slops by Use of Surfactant and Denitrifying Bacteria", Fine and Specialty Chemicals, vol. 14, No. 2, Jan. 21, 2006, pp. 19-22.

(Continued)

Primary Examiner — Louise W Humphrey
Assistant Examiner — Anjali Ajit Hirani
(74) Attorney, Agent, or Firm — Novick, Kim & Lee, PLLC; Allen Xue

(57) ABSTRACT

The present invention relates to the field of biotechnology, and discloses a composition capable of promoting the growth of denitrifying microorganisms and uses thereof. The composition contains a glycolipid, an alditol, and a salt of organic acid, wherein the glycolipid is at least one of trehalose glycolipid, sophorolipid and rhamnolipid. The composition provided in the present invention can promote the growth of denitrifying microorganisms, and thereby improve the denitrification activity of the denitrifying microorganisms, promote a smooth denitrification process, and shorten the processing time.

14 Claims, No Drawings

(56) References Cited

OTHER PUBLICATIONS

Lingxiao Gong et al.; "Performance of heterotrophic partial denitrification under feast-famine condition of electron donor: A case study using acetate as external carbon source", Bioresource Technology, vol. 133, 2013, pp. 263-269.

Yecheng Feng et al., "Study on Simultaneous Nitrification/Denitrification", Shanghai Environmental Sciences, vol. 21, No. 9, 2002, pp. 527-529, 579.

Aizhong Ding et al,; "Experimental Evidence for Aerobic Bacterial Denitrification Reaction" Chinese Science Bulletion, vol. 45, Mar. 2000. pp. 2779-2782.

* cited by examiner

COMPOSITION CAPABLE OF PROMOTING THE GROWTH OF DENITRIFYING MICROORGANISMS AND USES THEREOF

CROSS REFERENCE TO RELATED APPLICATIONS

This application claims priority to Chinese Application No. 201611073729.7, filed on Nov. 29, 2016, entitled "A Microorganism Cultivating Promoter for Denitrification and Uses Thereof", which is specifically and entirely incorporated by reference.

FIELD OF THE INVENTION

The present invention relates to the field of biotechnology, in particular to a composition capable of promoting the growth of denitrifying microorganisms and uses thereof.

BACKGROUND OF THE INVENTION

Denitrifying bacteria are a sort of facultative anaerobes that convert nitrate nitrogen or nitrite nitrogen into nitrogen. Usually, such microorganisms can be induced to produce nitrate reductase A and nitrite reductase required for a denitrification under anaerobic conditions, and thereby carry out denitrification with nitrate or nitrite as the electron acceptors. Since the environments required by the microorganisms are different, during the entire denitrification process for wastewater treatment (i.e., nitrification procedure and denitrification procedure), the impact resistant capability of the system is poor, the growth of nitrifying bacteria is inhibited by ammonia nitrogen and nitric nitrogen with high-concentration, and the growth of denitrifying bacteria is inhibited owing to high-concentration dissolved oxygen and inadequate carbon source; consequently, the overall denitrification is affected. However, at present, there is no effective method for obtaining denitrifying bacteria so as to use the obtained bacteria for denitrification in the nitrification and denitrification process for wastewater treatment.

In recent years, loss of total nitrogen was often found in many aerobic denitrification tanks that were in service (Yecheng FENG, et al., Study on Simultaneous Nitrification/Denitrification, Shanghai Environmental Sciences, 2002, Vol. 21). Many researchers and reports in China and other countries have proved the existence of aerobic denitrification (Aizhong DING, et al., Experimental Evidences on Aerobic Bio-Denitrification Reaction [J], Scientific News, 2000, Vol. 45). Therefore, with a denitrification technique developed utilizing aerobic denitrification bacteria, the denitrification process can be executed in a single reactor, and thereby the floor space and construction investment can be greatly reduced; the consumption of chemical substances for adjusting pH of the system and carbon sources can be reduced, the agent expense can be saved, and the operation cost can be reduced; the COD (chemical oxygen demand) can also be removed along with denitrification, so as to enhance the impact resistant capability of the system and improve the treatment effect.

CN1800053A has disclosed a method for nitrite denitrification with granular sludge. Though the method has advantages such as high sludge concentration in the system, high reactor efficiency, and simple process, etc., the denitrifying granular sludge can be obtained only after culturing for 30-90 days at 15-30, and the nitrogen concentration in nitrous acid in the treated wastewater is 10-200 mg/L. CN101898828A has disclosed a shortcut denitrifying granular sludge culturing method, which realizes enrichment and cultivation of denitrifying granular sludge through three stages in different culture media. CN105621611A has disclosed a denitrifier that utilizes nitrite for denitrification and use thereof. The invention mainly employs bacterial strains in a special combination at a specific mix ratio to realize denitrification and involves a variety of bacterial strains, and the preparation process is relatively complex. CN106754450A has described a denitrifying microorganism culturing promoter, which mainly comprises metal salts, polyamine, organic acid hydroxylamine, and salts of organic acid, and can promote the growth of denitrifying microorganisms and improve the treatment effect. However, the content of metal salts in the promoter is high, and may cause secondary pollution to water bodies if it is used in a long term.

SUMMARY OF THE INVENTION

To solve the problems of complex formulation or operation, and possibility of secondary pollution in the prior art, the present invention provides a composition capable of promoting the growth of denitrifying microorganisms (denitrifiers) and uses thereof.

To attain the object described above, in a first aspect, the present invention provides a composition capable of promoting the growth of denitrifying microorganisms, which contains a glycolipid, an alditol, and a salt of organic acid, wherein the glycolipid is at least one of trehalose glycolipid, sophorolipid and rhamnolipid.

In a second aspect, the present invention provides a culture medium capable of promoting the growth of denitrifying microorganisms, which contains a nitrate and/or a nitrite, and the composition described above.

In a third aspect, the present invention provides a method for culturing denitrifying microorganisms, which comprises: contacting a culture system that contains denitrifying microorganisms with a promoter, wherein the promoter is the composition described above; or inoculating the denitrifying microorganisms to the culture medium described above for culturing.

In a fourth aspect, the present invention provides a method for denitrification with denitrifying microorganisms, which comprises: contacting a denitrification system that contains denitrifying microorganisms with a promoter, wherein the promoter is the composition described above.

In a fifth aspect, the present invention discloses use of the above-mentioned composition in promoting the growth of denitrifying microorganisms and/or denitrification.

Through above-mentioned technical solution, the composition provided in the present invention can promote the growth of denitrifying microorganisms and thereby improve the denitrification activity of the denitrifying microorganisms, promote a smooth denitrification process, and shorten the processing time. Denitrifying microorganisms cultured with the composition provided in the present invention have high activity, high flocculence property, long service life, strong impact resistance and high salt tolerance properties. In addition, the formulation of the composition provided in the present invention is simple, and the composition is easy to prepare and will not cause secondary pollution to water bodies.

DETAILED DESCRIPTION OF THE EMBODIMENTS

The ends points and any value in the ranges disclosed in the present invention are not limited to the exact ranges or values; instead, those ranges or values shall be comprehended as encompassing values that are close to those ranges or values. For numeric ranges, the end points of the ranges, the values between end points of the ranges and the discrete point values, and the discrete point values may be combined to obtain one or more new numeric ranges, which shall be deemed as having been disclosed specifically in this document.

The composition capable of promoting the growth of denitrifying microorganisms provided in the present invention contains a glycolipid, an alditol, and a salt of organic acid, wherein the glycolipid is at least one of trehalose glycolipid, sophorolipid and rhamnolipid.

According to the present invention, the object of the present invention can be attained as long as the above-mentioned three constituents are used in combination, and there is no particular requirement for the mix ratio of those three constituents; for example, the weight ratio among the glycolipid, alditol and salt of organic acid may be (0.5-15):(0.5-15):(5-30), preferably (2-10):(2-10):(6-17). More preferably, the weight ratio of the glycolipid to the alditol is 1:(0.3-5), e.g., 1:0.3, 1:0.5, 1:0.6, 1:0.8, 1:1, 1:1.5, 1:2, 1:2.5, 1:3, 1:3.5, 1:4, 1:4.5, 1:5, or any value between them.

More preferably, the weight ratio of the glycolipid to the salt of organic acid is 1:(0.7-8.5), e.g., 1:0.7, 1:1, 1:1.3, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, or any value between them.

In the present invention, the glycolipid is a general term of the compounds in which a saccharide (carbohydrate) is bonded with a lipid through glycosidic bond via its hemi-acetal hydroxyl, and is usually generated through fermentation by microorganisms.

The trehalose glycolipid used in the present invention usually refers to glycolipid generated through fermentation by some microorganisms too.

The sophorolipid used in the present invention refers to a secondary metabolite generated by *Candida* through fermentation with a saccharide and a vegetable oil as carbon sources. It is composed of two moieties: hydrophilic sophorose (two glucose molecules being bonded through β-1,2 glycosidic bond) and hydrophobic saturated or unsaturated long-chain ω- (or ω-1) hydroxylated fatty acid. There are mainly two types of sophorolipids: lactone sophorolipid and acid sophorolipid.

The rhamnolipid used in the present invention is usually generated by *Pseudomonas* or *Burkholderia*. It is not a simplex structural body, but is a mixture of a variety of homogeneous structures. The fermentation product of *Pseudomonas* or *Burkholderia* usually contains 4 major types of rhamnolipids (R1-R4):

(R1)

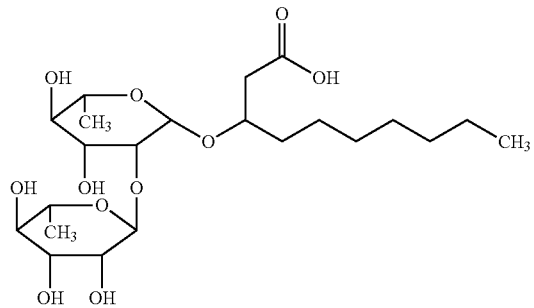

(R2)

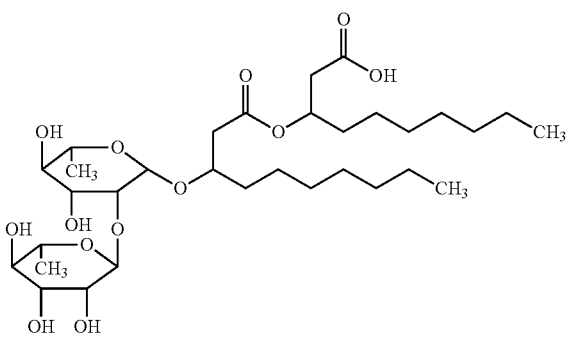

(R3)

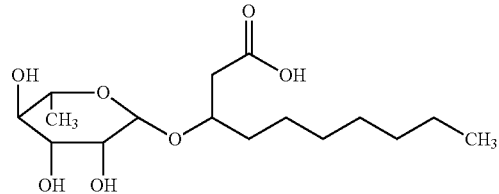

(R4)

According to a preferred embodiment of the present invention, the glycolipid is sophorolipid, more preferably lactone sophorolipid.

In the present invention, the alditol (sugar alcohol) is a product obtained after the carbonyl in saccharide (monosaccharide or disaccharide) is reduced. The alditol may be any common alditol in the art, preferably C4-C12 (e.g., C4, C5, C6, C7, C8, C9, C10, C11 or C12) alditol, more preferably selected from at least one of mannitol, xylitol, lactitol, sorbitol, ribitol, galactitol, inositol and erythritol, optimally lactitol.

In the present invention, the salt of organic acid may be any common salt of organic acid in the art, such as sodium salt of organic acid, preferably sodium salt of C2-C6 (e.g., C2, C3, C4, C5 or C6) organic carboxylic acid, more preferably selected from at least one of sodium acetate, sodium succinate and sodium citrate, optimally sodium acetate. The salt of organic acid is especially helpful for inducing nitrite reductase required for denitrification, so as to attain a good denitrification effect. In a particularly preferred embodiment of the present invention, the glycolipid is lactone sophorolipid, the alditol is lactitol, the salt of organic acid is sodium acetate, and the weight ratio among them is 1:(0.7-1.5):(2.5-3.5), more preferably 1:1:3.

According to the present invention, the composition may further contain an additive, wherein the ratio of the total weight of the glycolipid, alditol and salt of organic acid to the weight of the additive is 100:(10-20). Preferably, the additive is selected from at least one of polyamine, organic acid hydroxylamine, and $Na_2SO_3$. The additive is especially helpful for promoting the growth of denitrifying microorganisms and further improves the activity of nitrate reductase A and nitrite reductase at the same time.

The polyamine may be any aliphatic compound that contains two or more amino groups, and its carbon number may be 4-10 (e.g., 4, 5, 6, 7, 8, 9 or 10); more preferably, the polyamine is spermine and/or spermidine.

The organic acid hydroxylamine may be a substance formed by any organic acid (e.g., C1-C5 saturated monocarboxylic acid) and hydroxylamine ($H_2N$—OH) (which is generally a mixture or mixed solution of these two constituents, the molar ratio of the hydroxylamine to the organic acid (measured in carboxyl) may be 1:(0.5-2), e.g., 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1.1.9, 1.2, or any value between them). More preferably, the organic acid hydroxylamine is formic acid hydroxylamine and/or acetic acid hydroxylamine, i.e., the organic acid hydroxylamine is a mixture or mixed solution of formic acid and/or acetic acid, and hydroxylamine. In a case that the organic acid hydroxylamine is provided in the form of a mixed solution, the solvent may be water. The amount of the organic acid hydroxylamine involved in the present invention is measured in the total weight of the organic acid and hydroxylamine, excluding the amount of any possible existing solvent.

The composition provided in the present invention can promote the growth of denitrifying microorganisms without using any inorganic metal salt. Therefore, according to a preferred embodiment of the present invention, the content of inorganic metal salts in the composition is not higher than 0.01 wt %, more preferably the composition doesn't contain any inorganic metal salt. The composition provided in the present invention can promote the growth of denitrifying microorganisms. Therefore, the composition can be used in culturing process of denitrifying microorganisms, or can be directly added to an wastewater treatment system that includes a denitrification unit to improve the total nitrogen removal effect of the existing wastewater treatment system; or the composition may be used in denitrification treatment of salty wastewater; the composition may also be used in quick initiation of a denitrification process for an ammonia-containing system and quick recovery of a system that has suffered impacts.

The culture medium capable of promoting the growth of denitrifying microorganisms provided in the present invention contains nitrate and/or nitrite, and the composition described above.

The denitrifying microorganisms utilize nitrate and/or nitrite as electron acceptors to carry out respiration and obtain energy, and thereby realize denitrification. Therefore, the nitrate and/or nitrite can be any common inorganic nitrogen source that provides an electron acceptor for the denitrifying microorganisms. Usually, the ratio of the total weight of the nitrate and/or nitrite (calculated in N) to the weight of the composition is 1,000:(5-10), e.g., 1,000:5, 1,000:5.5, 1,000:6, 1,000:6.7, 1,000:7, 1,000:8, 1,000:9, 1,000:10, or any value between them.

The method for culturing denitrifying microorganisms provided in the present invention comprises: contacting a culture system that contains denitrifying microorganisms with a promoter, wherein the promoter is the composition described above;

or inoculating the denitrifying microorganisms to the culture medium described above for culturing (the culturing condition may be the same as the contacting condition).

The method for denitrification with denitrifying microorganisms provided in the present invention comprises: contacting a denitrification system that contains denitrifying microorganisms with a promoter, wherein the promoter is the composition described above. As described above, the denitrification system may be a denitrification system at any stage.

In the culturing method or denitrification method provided in the present invention, the dose of the promoter may be 0.01-10 mg/L, preferably 0.5-1 mg/L.

In the culturing method or denitrification method provided in the present invention, the contacting condition may be conventional condition; preferably, the contact condition include: 20-40° C. Preferably, the contact condition further include: pH 6-9. Furthermore, the contact condition preferably further include: 0.1-3 mg/L of dissolved oxygen. Wherein the dissolved oxygen is measured with an iodometric method.

Moreover, the present invention further provides an use of the composition in promoting the growth of denitrifying microorganisms and/or denitrification.

In the culturing method, denitrification method or use provided in the present invention, the denitrifying microorganisms may be common denitrifying microorganisms (usually bacteria) in the art. According to a preferred embodiment of the present invention, the denitrifying microorganism is selected from at least one of *Arthrobacter creatinolyticus, Flavobacterium mizutaii, Paracoccus denitrificans, Methylobacterium phyllosphaerae, Kocuria palustris,* and *Staphylococcus cohnii.*

Hereunder the present invention will be detailed in examples. In the following examples, the COD concentration is measured with the method specified in GB11914-89 "Water Quality—Determination of Chemical Oxygen Demand—Dichromate Method"; the ammonia nitrogen concentration is measured with the method specified in GB7478-87 "Water Quality—Determination of Ammonium—Distillation and Titration Method"; the concentration of nitrite nitrogen is measured with the method specified in GB7493-87 "Water Quality—Determination of Nitrite Nitrogen—Spectrophotometric Method"; the total nitrogen concentration is measured with the method specified in GB11894-89 "Water Quality—Determination of Total Nitrogen—UV Spectrophotometric Method—Alkaline Potassium Persulfate Digestion Method".

Preparation Examples 1-22

Compositions (or promoters) 1#-22# are prepared according to the compositions and mix ratios shown in Table 1:

TABLE 1

| Promoter | Glycolipid Name | Part by Weight | Alditol Name | Part by Weight | Salt of organic acid Name | Part by Weight |
|---|---|---|---|---|---|---|
| 1# | Lactone sophorolipid | 5 | Lactitol | 5 | Sodium acetate | 15 |
| 2# | Acid sophorolipid | 2 | Lactitol | 6 | Sodium acetate | 17 |
| 3# | Trehalose glycolipid | 7 | Lactitol | 7 | Sodium acetate | 11 |
| 4# | Rhamnolipid | 10 | Lactitol | 5 | Sodium acetate | 10 |
| 5# | Lactone sophorolipid | 2 | Mannitol | 10 | Sodium acetate | 8 |
| 6# | Lactone sophorolipid | 4 | Xylitol | 4 | Sodium acetate | 12 |
| 7# | Lactone sophorolipid | 6 | Ribitol | 6 | Sodium acetate | 8 |
| 8# | Lactone sophorolipid | 8 | Galactitol | 5 | Sodium acetate | 6 |
| 9# | Lactone sophorolipid | 10 | Inositol | 3 | Sodium acetate | 7 |
| 10# | Lactone sophorolipid | 5 | Erythritol | 5 | Sodium acetate | 10 |
| 11# | Lactone sophorolipid | 5 | Lactitol | 5 | Sodium citrate | 15 |
| 12# | Lactone sophorolipid | 5 | Lactitol | 5 | Sodium succinate | 15 |
| 13# | Lactone sophorolipid | — | Lactitol | 5 | Sodium acetate | 15 |
| 14# | Lactone sophorolipid | 5 | Lactitol | — | Sodium acetate | 15 |
| 15# | Lactone sophorolipid | 5 | Lactitol | 5 | Sodium acetate | — |
| 16# | Lactone sophorolipid | 15 | Lactitol | — | Sodium acetate | — |
| 17# | Lactone sophorolipid | — | Lactitol | 15 | Sodium acetate | — |
| 18# | Lactone sophorolipid | — | Lactitol | — | Sodium acetate | 15 |
| 19# | Lactone sophorolipid | 5 | Lactitol | 5 | Sodium malate | 15 |
| 20# | Lactone sophorolipid | 5 | Maltitol | 5 | Sodium acetate | 15 |
| 21# | Digalactosyl diglyceride | 5 | Lactitol | 5 | Sodium acetate | 15 |
| 22# | Lactone sophorolipid | 5 | Lactitol | 5 | Sodium chloride | 15 |

Example 1

This example is provided to describe the effect of the promoter in improving total nitrogen removal from a wastewater treatment system.

In a wastewater, the COD concentration is 450 mg/L, the ammonia nitrogen concentration is 150 mg/L. An anoxic-oxic (AO) process is used for the wastewater treatment, wherein the anaerobic condition is: dissolved oxygen <0.2 mg/L, pH=7.2-7.8, and temperature=28-32° C.; the aerobic condition is: dissolved oxygen=1-5 mg/L, pH=7.5-8, temperature=28-32° C., reflux ratio=3-5; After such treatment, the average COD concentration in the outputted water is 90 mg/L, the ammonia nitrogen ($NH_3$—N) concentration in the outputted water is lower than 15 mg/L, the total nitrogen (TN) concentration in the outputted water is as high as 70 mg/L, wherein the nitrite nitrogen ($NO_2$—N) concentration is 40 mg/L, which doesn't reach the standard via this treatment.

TABLE 2

| Promoter | COD in outputted water (mg/L) | $NH_3$—N in outputted water (mg/L) | TN in outputted water (mg/L) | $NO_2$—N in outputted water (mg/L) |
|---|---|---|---|---|
| 1# | 51.1 | 10.5 | 28.2 | 0.2 |
| 2# | 52.9 | 14.5 | 32.6 | 1.5 |
| 3# | 59.8 | 13.3 | 35.1 | 1.3 |
| 4# | 53.5 | 14.2 | 31.9 | 1.6 |
| 5# | 55.3 | 11.9 | 34.5 | 2.2 |
| 6# | 54.7 | 12.1 | 32.3 | 1.7 |
| 7# | 58.3 | 14.3 | 34.7 | 1.4 |
| 8# | 54.4 | 12.8 | 36.6 | 1.9 |
| 9# | 55.8 | 13.2 | 35.2 | 2.6 |
| 10# | 56.1 | 14.1 | 33.4 | 1.9 |
| 11# | 58.9 | 12.5 | 37.3 | 1.6 |
| 12# | 57.8 | 13.4 | 32.7 | 2.1 |
| 13# | 75.2 | 14.2 | 51.9 | 5.9 |
| 14# | 71.2 | 13.8 | 53.6 | 8.7 |
| 15# | 70.9 | 14.5 | 54.9 | 5.6 |
| 16# | 80.1 | 14.2 | 55.7 | 12.1 |
| 17# | 79.9 | 13.9 | 57.9 | 9.6 |
| 18# | 76.8 | 14.7 | 56.7 | 11.8 |
| 19# | 69.6 | 14.8 | 47.1 | 4.8 |
| 20# | 62.2 | 14.7 | 43.8 | 4.9 |
| 21# | 84.7 | 14.6 | 65.4 | 35.5 |
| 22# | 87.6 | 15.8 | 67.2 | 37.3 |

It can be seen from the data shown in Table 2: according to a preferred embodiment of the present invention, after the promoter is added, the initial COD concentration is further decreased to be lower than 60 mg/L, the total nitrogen concentration in the outputted water is lower than 40 mg/L, and the nitrite nitrogen concentration is lower than 5 mg/L. Any case that one of the constituents in the formulation is disused in the promoter, the total nitrogen concentration in the outputted water is higher than 40 mg/L, and the nitrite nitrogen concentration is higher than 5 mg/L. Thus, the promoter provided in the present invention can significantly improve the effect of total nitrogen removal from wastewater, which also proves that the promoter prepared in the present invention can promote the growth of denitrifying microorganisms and enhance the impact resistant capability of the denitrifying microorganisms.

Example 2

This example is provided to describe the effect of the promoter in improving total nitrogen removal from a wastewater treatment system.

The wastewater is treated according to the treatment process and operating condition described in example 1, but: an additive is added in a certain amount along with the promoter 1#. The composition, dose and final effect of the additive are shown in Table 3.

Wherein the formic acid hydroxylamine is obtained by mixing a formic acid and a hydroxylamine at 1:1 molar ratio; the acetic acid hydroxylamine is obtained by mixing an acetic acid and a hydroxylamine at 1:1 molar ratio; both of them are prepared immediately after they are prepared.

TABLE 3

| Additive(s) | Dose (mg/L) | COD in outputted water(mg/L) | $NH_3$—N in outputted water(mg/L) | TN in outputted water(mg/L) | $NO_2^-$N in outputted water(mg/L) |
|---|---|---|---|---|---|
| Spermine | 0.10 | 47.9 | 9.3 | 21.3 | 0.1 |
| Spermidine | 0.10 | 48.4 | 8.9 | 23.9 | 0.2 |
| Formic acid hydroxylamine | 0.10 | 47.6 | 7.6 | 24.4 | 0.1 |
| Acetic acid hydroxylamine | 0.10 | 48.1 | 9.1 | 22.7 | 0.2 |
| $Na_2SO_3$ | 0.10 | 44.3 | 10.0 | 18.2 | 0.2 |
| Spermine + Formic acid hydroxylamine (1:1, wt) | 0.05 | 43.7 | 8.7 | 19.6 | 0.2 |
| Spermidine + Acetic acid hydroxylamine + $Na_2SO_3$ (1:1:1, wt) | 0.05 | 40.5 | 5.2 | 14.7 | 0.1 |

It can be seen from Table 3: as the additive is added, the COD concentration is further decreased to be lower than 50 mg/L, the total nitrogen concentration in the outputted water is lower than 25 mg/L, and the nitrite nitrogen concentration is lower than 1.0 mg/L; thus, the treatment effect is further improved.

Example 3

This example is provided to describe the effect of the promoter in improving total nitrogen removal and flocculation in a wastewater treatment system.

In a salty wastewater, the COD concentration is 400 mg/L, the ammonia nitrogen concentration is 150 mg/L, the total nitrogen concentration is 200 mg/L, the TDS (total dissolved solids) is 5,500 mg/L. An anaerobic and aerobic AO process is used for the wastewater treatment, wherein the anaerobic condition is: dissolved oxygen<0.2 mg/L, pH=7-7.5, and temperature=25-35° C.; the aerobic condition is: dissolved oxygen=1-5 mg/L, pH=7.5-8, temperature=25-35° C.; owing to high salinity in the wastewater, the treated wastewater doesn't reach the standard via this treatment; after treatment, the average COD concentration in the outputted water is 60 mg/L, the ammonia nitrogen ($NH_3$—N) concentration in the outputted water is 15-30 mg/L, the total nitrogen (TN) concentration in the outputted water is 80-110 mg/L, and the settlement ratio of sludge in 30 minutes $SV_{30}$ is 70%. Through analysis, it is found that there are large quantity of microorganisms for removing COD and microorganisms for removing ammonia nitrogen in the original AO system, but the denitrifying microorganisms for removing total nitrogen are inadequate; consequently, the nitrogenous pollutants can't be treated as per the standard. After the promoter 1# prepared in the preparation example is added to the tank A for 10 days so that the promoter concentration in the wastewater is maintained at 0.5 mg/L every day, through sampling and analysis for consecutive 5 days, it is found that the COD concentration in the outputted water is about 55 mg/L, the ammonia nitrogen concentration is lower than 8 mg/L, the total nitrogen concentration is lower than 40 mg/L, and the settlement ratio of sludge in 30 minutes $SV_{30}$ is decreased to 50%. Thus, it can be seen that the salty wastewater is treated standardly after the promoter is added, and the flocculence of the sludge is improved.

Example 4

This example is provided to describe the effect of the promoter in promoting the growth and salt tolerance of denitrifying microorganisms.

(1) *Kocuria palustris* (FSDN-A, CGMCC NO. 5061, see CN103103141A), *Staphylococcus cohnii* (FSDN-C, CGMCC NO. 5062, see CN103103142A), *Arthrobacter creatinolyticus* (FDN-1, CGMCC No. 3657, see CN102465105A), *Flavobacterium mizutaii* (FDN-2, CGMCC No. 3659, see CN102465106A), *Paracoccus denitrificans* (DN-3, CGMCC No. 3658, see CN102465104A) and *Methylobacterium phyllosphaerae* (SDN-3, CGMCC No. 3660, see CN102465103A) are cultured with the culture media shown in Table 4 under the following culturing condition respectively: temperature=30-35° C., pH=7.0-8.0, and dissolved oxygen=1-3 mg/L. The number of bacteria in the culture fluid is measured (via a plate colony counting method) and the TDS in the culture system is also determined (with a weighting method) after 48 h. The results are shown in Table 4.

TABLE 4

| Name of bacterial strain | Formulation of culture medium | Culturing time, h | Number of bacteria colonies/L | TDS in culture system, mg/L |
|---|---|---|---|---|
| FSDN-A | Beef extract: 10 g/L, peptone: 15 g/L, $NaNO_2$: 1.0 g/L, $KNO_3$: 0.8 g/L | 48 | $1.5 \times 10^9$ | 4000 |
| FSDN-C | Beef extract: 10 g/L, peptone: 15 g/L, $NaNO_2$: 1.0 g/L, methanol: 1.0 mL/L | 48 | $1.6 \times 10^9$ | 4000 |
| FDN-1 | Beef extract: 5 g/L, peptone: 10 g/L, $NaNO_2$: 1 g/L | 48 | $1.7 \times 10^9$ | 3000 |
| FDN-2 | Beef extract: 5 g/L, peptone: 10 g/L, $NaNO_2$: 1 g/L | 48 | $1.8 \times 10^9$ | 3000 |
| DN-3 | $KNO_3$: 1 g/L, sodium succinate: 8 g/L, $KH_2PO_4$: 1 g/L, $FeCl_2$: 0.5 g/L | 48 | $0.9 \times 10^9$ | 3000 |
| SDN-3 | $KNO_3$: 1.0 g/L, methanol: 0.75 mL/L, $KH_2PO_4$: 1 g/L, $FeCl_2$: 0.5 g/L | 48 | $1.0 \times 10^9$ | 3000 |

(2) The above bacterial strains are cultured with the method described in step (1), but the promoter 1# is further added into the culture media at a dose of 0.5 mg/L. The number of bacteria and the TDS in the culture fluid are measured after 36 h. The results are shown in Table 5.

TABLE 5

|   | Culturing time, h | Number of bacteria, colonies/L | TDS in culture system, mg · $L^{-1}$ |
| --- | --- | --- | --- |
| FSDN-A | 36 | $1.6 \times 10^9$ | 10000 |
| FSDN-C | 36 | $1.6 \times 10^9$ | 10000 |
| FDN-1 | 36 | $1.7 \times 10^9$ | 8000 |
| FDN-2 | 36 | $1.8 \times 10^9$ | 8000 |
| DN-3 | 36 | $1.0 \times 10^9$ | 5000 |
| SDN-3 | 36 | $1.1 \times 10^9$ | 5000 |

It can be seen from comparison between the results shown in Table 4 and Table 5: the promoter provided in the present invention not only can promote the growth of *Kocuria palustris, Staphylococcus cohnii, Arthrobacter creatinolyticus, Flavobacterium mizutaii, Paracoccus denitrificans*, and *Methylobacterium phyllosphaerae*, but also can improve the TDS tolerance of the microorganisms (i.e., improve salt tolerance thereof).

While the present invention is described above in detail in some preferred embodiments, the present invention is not limited to those embodiments. Various simple variations, including combinations of the technical features in any other appropriate way, can be made to the technical solution of the present invention within the scope of the technical concept of the present invention, and such variations and combinations shall be deemed as disclosed content in the present invention and falling into the protection scope of the present invention.

The invention claimed is:

1. A composition consisting of a glycolipid, an alditol, a salt of organic acid, less than or equal to 0.01 wt % inorganic metal salt, and optionally an additive, wherein the glycolipid is chosen from trehalose glycolipid, sophorolipid, rhamnolipid, or mixtures thereof, where the weight ratio among the glycolipid, the alditol, and the salt of organic acid is (0.5-15):(0.5-15):(5-30), and wherein the additive is chosen from polyamine, organic acid hydroxylamine, $Na_2SO_3$, or mixtures thereof.

2. The composition according to claim 1, wherein the weight ratio among the glycolipid, the alditol, and the salt of organic acid is (2-10):(2-10):(6-17).

3. The composition according to claim 1, wherein the glycolipid is sophorolipid; and/or, the alditol is C4-C12 alditol; and/or the salt of organic acid is C2-C6 sodium salt of organic acid.

4. The composition according to claim 1, wherein the glycolipid is lactone sophorolipid; and/or the alditol is chosen from mannitol, xylitol, lactitol, sorbitol, ribitol, galactitol, inositol, erythritol, or mixtures thereof; and/or the salt of organic acid is chosen from sodium acetate, sodium succinate, sodium citrate, or mixtures thereof.

5. The composition according to claim 1, wherein the ratio of a total weight of the glycolipid, the alditol, and the salt of organic acid to a weight of the additive is 100:(10-20).

6. The composition according to claim 5, wherein the polyamine is spermine, spermidine, or a mixture thereof; and/or the organic acid hydroxylamine is formic acid hydroxylamine, acetic acid hydroxylamine, or a mixture thereof.

7. The composition according to claim 1, wherein the composition is absent of an inorganic metal salt.

8. A method for denitrification, comprising:
preparing a composition of claim 1;
mixing the composition of claim 1 into a waste water that contains denitrifying microorganisms and one or more compounds containing nitrogen; and
obtaining a denitrified waste water.

9. The method of claim 8, wherein a dosage of the composition of claim 1 in the waste water is 0.01-10 mg/L.

10. The method of claim 9, wherein the dosage of the composition of claim 1 in the waste water is 0.5-1 mg/L.

11. The method of claim 8, wherein the mixing step is carried out at 20-40° C. and pH of 6-9.

12. The method of claim 8, wherein the waste water has 0.1-3 mg/L of dissolved oxygen.

13. The composition according to claim 1, wherein the glycolipid is lactone sophorolipid, the alditol is chosen from mannitol, lactitol, sorbitol, ribitol, galactitol, inositol, erythritol, or mixtures thereof, and the salt of organic acid is sodium acetate.

14. The composition according to claim 1, wherein the glycolipid is lactone sophorolipid, the alditol is lactitol, and the salt of organic acid is sodium acetate.

* * * * *